United States Patent [19]

Lederman et al.

[11] Patent Number: 5,368,842
[45] Date of Patent: Nov. 29, 1994

[54] HIGH EFFICACY AEROSOL ANTIPERSPIRANT COMPOSITION

[75] Inventors: Barry P. Lederman, Hyde Park; David T. Callaghan, Foxborough, both of Mass.

[73] Assignee: The Gillette Company, Boston, Mass.

[21] Appl. No.: 968,552

[22] Filed: Oct. 29, 1992

[51] Int. Cl.⁵ ............................ A61K 7/38; A61K 9/12
[52] U.S. Cl. ........................................ 424/47; 424/68
[58] Field of Search ........................ 424/46, 47, 68

[56] References Cited

U.S. PATENT DOCUMENTS

| | | | |
|---|---|---|---|
| 3,014,844 | 12/1961 | Thiel et al. | 424/46 |
| 3,081,223 | 3/1963 | Gunning et al. | 424/46 |
| 3,088,874 | 5/1963 | Geary et al. | 424/47 |
| 3,124,505 | 3/1964 | Doyle et al. | 424/46 |
| 3,218,263 | 11/1965 | Doyle et al. | 424/46 |
| 3,873,686 | 3/1975 | Beekman | 424/46 |
| 3,920,807 | 11/1975 | Curry et al. | 424/47 |
| 4,359,456 | 11/1982 | Gosling et al. | 424/68 |
| 4,477,431 | 10/1984 | Suffis et al. | 424/66 |
| 4,840,786 | 6/1989 | Johnson | 424/43 |
| 4,863,721 | 9/1989 | Beck | 424/47 |
| 4,904,463 | 2/1990 | Johnson | 424/44 |
| 4,935,224 | 6/1990 | Russo | 424/47 |
| 5,082,652 | 1/1992 | Mayfield | 424/47 |
| 5,156,834 | 10/1992 | Beckmeyer et al. | 424/65 |

FOREIGN PATENT DOCUMENTS

| | | | |
|---|---|---|---|
| 183171 | 6/1986 | European Pat. Off. | 424/68 |
| 274252 | 7/1988 | European Pat. Off. | 424/68 |
| 319168 | 6/1989 | European Pat. Off. | 424/66 |
| 337464 | 10/1989 | European Pat. Off. | 424/68 |
| 405598 | 1/1991 | European Pat. Off. | 424/68 |
| 1467676 | 3/1977 | United Kingdom | 424/47 |
| 2048229 | 12/1980 | United Kingdom | 424/68 |

Primary Examiner—Dale R. Ore
Attorney, Agent, or Firm—Stephan P. Williams

[57] ABSTRACT

The present invention embraces an aerosol antiperspirant composition which comprises a suspension of about 5 to 15% high efficacy aluminum salt in powder form in about 15 to 35% volatile silicone and about 40 to 80% liquefied hydrocarbon propellant with about 0.7 to 1.5% hydrophobic colloidal silica suspending agent and about 0.15 to 0.35% hydrophilic colloidal silica suspending agent. The composition of the present invention has superior antiperspirant efficacy and avoids the use of materials which have an adverse effect on efficacy, namely oil soluble emollient esters such as isopropyl myristate and polar agents such as ethanol.

13 Claims, No Drawings

HIGH EFFICACY AEROSOL ANTIPERSPIRANT COMPOSITION

BACKGROUND OF THE INVENTION

This invention relates to an aerosol antiperspirant composition with high efficacy and improved stability.

It is known that the antiperspirant efficacy of aluminum chlorhydrate salts can be significantly improved by heat ageing aluminum chlorhydrate solutions under certain conditions. In this regard, see for example, GB 2,048,229 and U.S. Pat. No. 4,359,456, which are incorporated herein by reference. Thus, it is generally known that heating a solution of aluminum chlorhydrate of relatively low concentration (generally under 20% and preferably about 10%) at a temperature above 50° C. (preferably about 80° C.) for a significant period of time (typically 16 hours or more) will shift the form of the aluminum species present in the composition to a much more efficacious form. This highly efficacious form is unstable in solution and must be rapidly dried after conversion in order to obtain a high efficacy aluminum chlorhydrate salt. This salt, when reconstituted as a 10% aqueous solution and promptly subjected to size exclusion chromatography, preferably HPLC, will produce two successive peaks containing at least 80% of the aluminum present in the composition, wherein the ratio of the latter of said peaks, which is referred to as peak 4, to the former of said peaks, which is referred to as peak 3, is at least 1.0 with respect to height and at least 0.70 with respect to area.

It is also known that an antiperspirant salt may be conveniently formulated in aerosol form by suspending from 1 to 20% of powdered aluminum chlorhydrate in 1 to 25% of a carrier liquid along with 0.1 to 5% of a suspending agent and 50 to 95% of a propellant. See, for example, EP 274,252, GB 1,467,676 and U.S. Pat. No. 4,359,456. Typical carrier vehicles include cyclomethicone (volatile cyclic silicone) and isopropyl myristate, typical propellants include hydrocarbons and halogenated hydrocarbons, and typical suspending agents include hydrophobic clays, such as Bentone 38, and hydrophilic colloidal silicas such as Aerosil 200 and Cab-O-Sil M-5. Such aerosol formulations also often contain small amounts of a lower alkanol, such as ethanol, or some other polar agent, such as propylene carbonate, to interact with the clay suspending agent to improve the suspending properties.

When halogenated hydrocarbon propellants were replaced by hydrocarbon propellants, it became more difficult to formulate high quality aerosol antiperspirants. The need for a good suspending agent became much more critical in view of the much lower density of the hydrocarbon propellant versus the halogenated hydrocarbon propellant and not all of the previously utilized suspending agents were suitable for use in such aerosol formulations. For example, hydrophilic silica caused excessive viscosity build-up in processing concentrates containing cyclomethicone. Therefore, in such formulations the suspension system of choice was a quaternium hectorite hydrophobic clay (e.g., Bentone 38) in conjunction with a small amount of a polar additive (e.g., ethanol).

It has now been discovered that certain materials commonly used in traditional aerosol antiperspirant formulations have an adverse effect on antiperspirant efficacy, and particularly on the stability of high efficacy antiperspirant salts formulated as an aerosol composition. It has been further discovered that the efficacy of an aerosol antiperspirant formulation can be significantly improved and maintained at that level for a long period of time by removing those agents which have an adverse impact on efficacy.

One of the materials which has an adverse effect on efficacy includes oil soluble emollient esters, that is high molecular weight esters commonly used as emollients. These esters particularly include the fatty acid esters, especially isopropyl myristate. Another one of the materials which has an adverse effect on efficacy includes polar materials such as lower alkanols, especially ethanol. While the presence of polar materials has no effect on conventional aluminum chlorhydrate salts, it has been found that when even small quantities as low as 1% are present in a composition containing a high efficacy aluminum chlorhydrate salt, the salt tends to revert from the high efficacy aluminum species toward the conventional form. This conversion is readily seen in HPLC chromatograms of the salt, where the peak 4 to peak 3 area ratio diminishes with time.

Since polar materials such as ethanol are often used in conjunction with conventional hydrophobic clay suspending agents, such as Bentone 38, to improve their suspension characteristics, the elimination of such polar agents in order to maintain efficacy requires that a different suspension system must be found to adequately formulate a high efficacy aerosol antiperspirant composition.

It is an object of the present invention to develop an aerosol antiperspirant composition with high antiperspirant efficacy. It is also an object to develop a high efficacy aerosol antiperspirant composition whose efficacy does not deteriorate with time. It is a further object to develop a high efficacy aerosol antiperspirant composition with a suspension system that provides advantageous suspension properties and good processing characteristics. It is also a further object to develop a high efficacy aerosol antiperspirant composition with all of the aforementioned characteristics and, in addition, with a low level of hydrocarbon propellant that meets California Air Resources Board environmental standards.

SUMMARY OF THE INVENTION

The present invention embraces an aerosol antiperspirant composition which comprises a suspension of about 5 to 15% high efficacy aluminum salt in powder form in about 15 to 35% volatile silicone and about 40 to 80% liquefied hydrocarbon propellant with about 0.7 to 1.5% hydrophobic colloidal silica suspending agent and about 0.15 to 0.35% hydrophilic colloidal silica suspending agent. The composition of the present invention has superior antiperspirant efficacy and avoids the use of materials which have an adverse effect on efficacy, namely oil soluble emollient esters such as isopropyl myristate and polar agents such as ethanol.

DETAILED DESCRIPTION OF THE INVENTION

Figure 1:
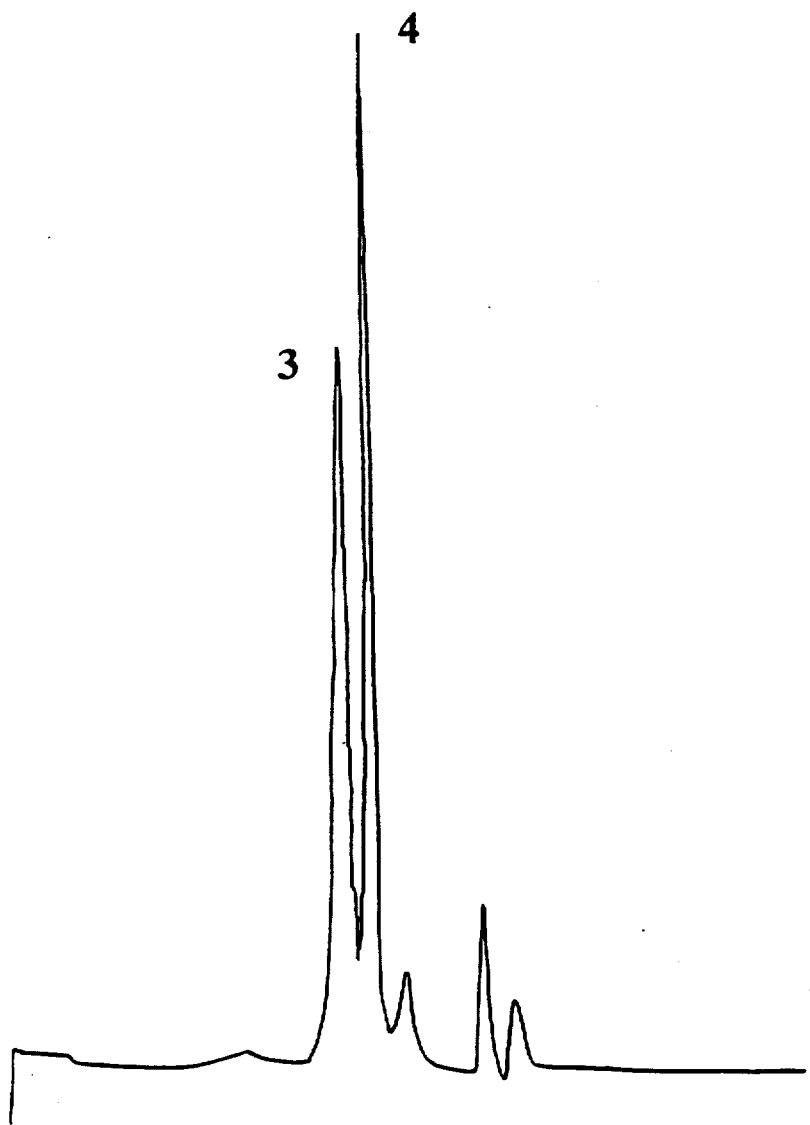
FIG. 1 depicts an HPLC chromatogram of a typical high efficacy aluminum chlorhydrate salt freshly dissolved as a 10% aqueous solution with peaks 3 and 4 identified.

The high efficacy aluminum salt which is utilized in the aerosol antiperspirant composition of the present invention has the basic formula $Al_2(OH)_{6-a} X_a \cdot nH_2O$ wherein X is Cl, Br, I or $NO_3$, a is 0.3 to 4, preferably 1 to 2, such that the Al to X mole ratio is about 1/1 to 2.1/1, and n is 1 to 6, preferably about 2. Most preferably, the aluminum salt is aluminum chlorhydrate (i.e., X is Cl) and a is about 1, such that the aluminum to chlorine mole ratio is about 1.9/1 to 2.1/1. The amount of aluminum salt utilized in the aerosol composition will typically range from about 5 to 15%, preferably about 6 to 12%, and most preferably about 8 to 10%. The aluminum salt may be utilized in the form of a controlled particle size, typically 10–50µ, or in the form of an impalpable powder.

The aforementioned aluminum salts are utilized in their high efficacy forms as described, for example, in GB 2,048,229, U.S. Pat. No. 4,359,456, EP 337,464 and EP 405,598. While there are a variety of ways to obtain high efficacy aluminum salts, it is preferred to make them by heating an approximately 10% aqueous solution of aluminum salt at about 80° C. for about 16 hours, rapidly concentrating the solution to about 50% concentration, then immediately spray drying. It is most preferred to conduct the aforedescribed heating step for about 20 hours at 87° C., then rapidly concentrating to 35% concentration followed by spray drying.

The first of the aforedescribed methods produces high efficacy aluminum chlorhydrate which, when reconstituted as a 10% aqueous solution, produces an HPLC chromatogram like that shown in FIG. 1, wherein the ratio of the area under peak 4 to the area under peak 3 is about 0.82. The second and most preferred method described above produces a very high efficacy aluminum chlorhydrate which, when reconstituted as a 10% aqueous solution, produces an HPLC chromatogram similar to that shown in FIG. 1, except that the ratio of the area under peak 4 to the area under peak 3 is about 1.0.

Thus, the term high efficacy aluminum salt, as used in this specification, is intended to embrace aluminum salts which, when reconstituted as a 10% aqueous solution and promptly subjected to high performance liquid chromatography (HPLC.), produce an HPLC chromatogram similar to that shown in FIG. 1, wherein at least 80% of the aluminum is contained in two successive peaks, which peaks are conveniently labelled peaks 3 and 4 (representing $Al^c$ and $Al^{c'}$), and the ratio of the area under peak 4 to the area under peak 3 is at least 0.70. Preferred are aluminum salts which have an HPLC peak 4 to peak 3 area ratio of at least 0.80, and most preferred are salts with an HPLC peak 4 to peak 3 area ratio of at least 1.0.

While any of a wide variety of conventional HPLC techniques may be utilized to produce a chromatogram which resolves the predominant aluminum species into two successive peaks, like the chromatogram shown in FIG. 1, the HPLC technique which produced FIG. 1 is a convenient one and was carried out under the following conditions:

Sample size: 1.0 µL as 10% aqueous solution (measured within 2 hours of makeup)
Column: 4.6 mm × 50 cm stainless steel packed with Nucleosil 100-5 (porous spherical silica particles approximately 5 µm in diameter having a pore diameter of 10 nm)
Eluent: 0.01M aqueous nitric acid
Flow rate: 0.5 ml/minute
Detector: refractive index Following the above HPLC technique, peaks 3 and 4, as shown in FIG. 1, appear at retention times of Kd=0.32–0.38 and Kd=0.49–0.53 respectively. Naturally, of course, other HPLC techniques which use different column materials, eluents and flow rates will likely place peaks 3 and 4 in slightly different locations in the chromatogram, but the peak 4 to peak 3 area ratio can nonetheless be measured so long as the peaks are adequately resolved. Thus, the reference herein to a chromatogram similar to FIG. 1 does not mean identical to FIG. 1, but simply means a chromatogram which resolves peaks 3 and 4 in a manner like that shown in FIG. 1.

The carrier vehicle utilized in the aerosol antiperspirant composition of the present invention may be any conventional volatile silicone, including linear and cyclic siloxanes having an average of from 2 to 7 silicon atoms, preferably from 3 to 5 silicon atoms. Preferred are the volatile cyclic silicones, also known as cyclomethicones. The preferred cyclomethicone is DC-344 available from Dow Corning Corporation, which is a mixture of cyclic siloxanes having 3 to 5 silicon atoms. The amount of volatile silicone utilized in the composition may be varied within reasonable limits without detracting from the aesthetics or performance of the composition. Generally, the amount of volatile silicone may range from about 15 to 35% by weight of the total composition, preferably from about 24 to 30%.

The propellant utilized in the aerosol antiperspirant composition of the present invention may be selected from any of the conventional hydrocarbon propellants or mixtures thereof having a vapor pressure of at least 17 psig, preferably at least 25 psig, and most preferably at least 30 psig at 21° C. These hydrocarbon propellants typically include propane, n-butane, isobutane and cyclopropane, and mixtures thereof. Isobutane, used singly or admixed with other hydrocarbons, is preferred. Most preferred is propellant 31, which is a mixture of isobutane and small amounts of propane and n-butane, having a vapor pressure of 31 psig at 21° C. The propellant may also optionally include some halohydrocarbon, such as 1,1-difluoroethane and 1-chloro-1,1-difluoroethylene.

The suspension system utilized in the aerosol antiperspirant composition of the present invention is unique to aerosol systems and provides excellent suspension characteristics without the need for polar additives while maintaining desirable processing characteristics. The suspension system of the present invention includes two colloidal silica suspending agents in combination-one hydrophilic and one hydrophobic. While each of these suspending agents is well-known, it is not believed that they have been used in combination in aerosol antiperspirant compositions, particularly those containing volatile silicone and hydrocarbon propellant.

The hydrophilic colloidal silica contains silanol groups on the surface and is easily wetted with water. The hydrophobic colloidal silica contains hydrophobic groups on the surface such as

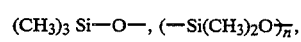

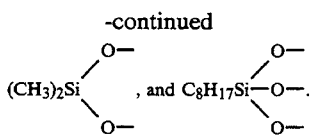

Useful hydrophilic colloidal silicas include Aerosil 130, Aerosil 150, Aerosil 200, Aerosil 300 and Aerosil 380 available from Degussa Corporation, and Cab-O-Sil fumed silica and Cab-O-Sil HS-5 available from Cabot Corporation. Preferred is Aerosil 300. which has a BET surface area of about 300 m²/gm. Useful hydrophobic colloidal silicas include Aerosil R202, Aerosil R805, Aerosil R812, Aerosil R972 and Aerosil R976 available from Degussa Corporation, and Cab-O-Sil TS-530 available from Cabot Corporation. Aerosil R972 which has a BET surface area of about 110 m²/gm with about 70% of the surface hydroxyl groups methylated, is preferred.

The hydrophilic colloidal silica is used in amounts of about 0.15 to 0.35%, preferably about 0.25%, in the present composition. The hydrophobic colloidal silica is used in amounts of about 0.7 to 1.5%, preferably about 1%.

It is preferred that the aerosol antiperspirant composition of the present invention contains substantially no lower alkanol, such as ethanol, or other polar additive such as propylene carbonate or water (in addition to water normally present as water of hydration bound to the aluminum salt). It is also preferred that the composition contains substantially no fatty acid esters, such as isopropyl myristate, or other oil soluble emollient esters, such as dibutyl phthalate.

The following example illustrates the present invention, with all parts and percentages by weight.

EXAMPLE

A high efficacy aluminum chlorhydrate salt manufactured by heat ageing a 10% aluminum chlorhydrate solution at 80° C. for 16 hours, concentrating to 50%, then immediately spray drying, produced a salt having the HPLC chromatogram shown in FIG. 1 with a peak 4 to peak 3 area ratio of 0.82.

An aerosol concentrate (no propellant) containing this salt was made up with the following components:

| | |
|---|---|
| aluminum chlorhydrate | 23.51 |
| cyclomethicone (DC-344) | 68.44 |
| talc | 4.95 |
| hydrophobic silica (Aerosil R972) | 2.48 |
| hydrophilic silica (Aerosil 300) | 0.62 |

This concentrate was allowed to stand 60 days at ambient conditions, then the aluminum salt was extracted to determine if there was any loss in efficacy. This salt produced an HPLC chromatogram virtually identical to that shown in FIG. 1, with a peak 4 to peak 3 area ratio of 0.83.

A portion of the above-described concentrate was formulated into finished aerosol units fourteen days after the concentrate was made. The finished aerosol unit had the following composition:

| | |
|---|---|
| propellant 31 | 59.20 |
| aluminum chlorhydrate | 9.50 |
| cyclomethicone (DC-344) | 27.65 |
| talc | 2.00 |
| hydrophobic silica (Aerosil R972) | 1.00 |
| hydrophilic silica (Aerosil 300) | 0.25 |
| fragrance | 0.40 |

The finished aerosol unit was aged forty-six days at room temperature, the contents expelled, and the aluminum salt extracted to determine if there was any loss in efficacy. This salt produced an HPLC chromatogram virtually identical to that shown in FIG. 1, with a peak 4 to peak 3 area ratio of 0.82.

The consistency in the HPLC chromatograms as described above confirms that the high efficacy aluminum salt maintains its efficacy when formulated in the aerosol concentrate and finished aerosol formulations of the present invention. That is, the other components of these formulations do not have an adverse effect on the aluminum salt efficacy during normal storage.

The above example can be repeated using an aluminum chlorhydrate salt manufactured by heat ageing a 10% aluminum chlorhydrate solution at 87° C. for 20 hours, concentrating to 35%, then immediately spray drying. This salt will produce an HPLC chromatogram similar to FIG. 1 with a peak 4 to peak 3 area ratio of about 1.00. This salt will also show no deterioration in efficacy as shown by HPLC, when formulated into aerosol concentrate and finished aerosol units as described above. The finished aerosol unit would be expected to achieve an absolute sweat reduction of about 44% in a standard sweat reduction test.

COMPARATIVE EXAMPLE

An aerosol concentrate and finished aerosol units were made up in the same manner as described above, but wherein the components making up the composition were selected so as to provide a finished aerosol unit with the following composition:

| | |
|---|---|
| aluminum chlorhydrate | 6.80 |
| cyclomethicone (DC-344) | 10.72 |
| isopropyl myristate | 2.00 |
| quaternium-18 hectorite (Bentone 38) | 1.00 |
| ethanol SD-40A | 2.00 |
| fragrance | 0.60 |
| propellant 31 | 76.88 |

The aluminum salt prior to formulation produced an HPLC chromatogram similar to FIG. 1 with a peak 4 to peak 3 area ratio of 0.83. After ageing the concentrate three months, the salt was extracted and produced an HPLC chromatogram in which the peak 4 to peak 3 area ratio dropped to 0.55. Similarly, after ageing the finished aerosol unit for three months, the extracted salt produced an HPLC chromatogram in which the peak 4 to peak 3 area ratio dropped to 0.67. It is believed that the significant deterioration in the amount of high efficacy aluminum species, as shown by the peak 4 to peak 3 ratio, is due to the small amount of ethanol present in the formulation. When measured in a standard sweat reduction test, this aerosol formulation provided an absolute sweat reduction of 33%. This is about 11 points less, in absolute sweat reduction points, than the preferred formulation described previously, which means that the preferred formulation of the present invention is about 33% more efficacious than the one described in this comparative example. It is believed that this significant increase in efficacy is due to four major factors: (1)

removal of isopropyl myristate; (2) removal of alcohol; (3) use of more efficacious aluminum salt; and (4) use of greater amount of aluminum salt.

What is claimed is:

1. An aerosol antiperspirant composition comprising by weight in suspension about 5 to 15% high efficacy aluminum antiperspirant salt in powder form, about 15 to 35% volatile silicone, about 40 to 80% liquefied hydrocarbon propellant with a vapor pressure of at least 17 psig at 21° C., about 0.7 to 1.5% hydrophobic colloidal silica suspending agent, and about 0.15 to 0.35% hydrophilic colloidal silica suspending agent, wherein said composition contains substantially no lower alkanol.

2. The aerosol antiperspirant composition of claim 1 comprising about 6 to 12% high efficacy aluminum chlorhydrate, about 24 to 30% of volatile cyclic silicone, and about 50 to 70% of liquefied hydrocarbon propellant with a vapor pressure of at least 25 psig at 21° C., wherein said composition contains substantially no fatty acid esters.

3. The aerosol antiperspirant composition of claim 2 comprising about 58 to 62% liquefied hydrocarbon propellant, wherein said composition contains substantially no added polar agents or oil soluble emollient esters.

4. The aerosol antiperspirant composition of claim 3 comprising about 8 to 10% high efficacy aluminum chlorhydrate, about 1% hydrophobic colloidal silica suspending agent and about 0.25% hydrophilic colloidal silica suspending agent.

5. The aerosol antiperspirant composition of claim 4 additional comprising about 1 to 4% talc and about 0 to 1.5% fragrance.

6. The aerosol antiperspirant composition of claim 5 wherein the high efficacy aluminum chlorhydrate which is utilized therein, when dissolved as a 10% aqueous solution, provides an HPLC chromatogram similar to that shown in FIG. 1 wherein peaks 3 and 4 contain at least 80% of the aluminum in the composition and the ratio of the area under peak 4 to the area under peak 3 is at least 0.70.

7. The aerosol antiperspirant composition of claim 6 wherein the ratio of the area under peak 4 to the area under peak 3 is at least 1.0.

8. The aerosol antiperspirant composition of claim 7 consisting essentially of about 9.5% high efficacy aluminum chlorhydrate, about 27.65% cyclomethicone DC-344, about 59.2% hydrocarbon propellant 31, about 2% talc, about 1% hydrophobic colloidal silica having a BET surface area of about 110 $m^2/gm$ with about 70% of the surface hydroxyl groups methylated, about 0.25% hydrophilic colloidal silica having a BET surface area of about 300 $m^2/gm$, and about 0.4% fragrance.

9. The aerosol antiperspirant composition of claim 1 wherein said composition contains substantially no added polar agents or oil soluble emollient esters.

10. The aerosol antiperspirant composition of claim 9 wherein said hydrophobic colloidal silica has a BET surface area of about 110 $m^2/gm$. with about 70% of the surface hydroxyl groups methylated and said hydrophilic colloidal silica has a BET surface area of about 300 $m^2/gm$.

11. In an aerosol antiperspirant composition comprising a high efficacy aluminum antiperspirant salt in powder form, a volatile silcone, liquefied hydrocarbon propellant and a suspending agent, the improvement wherein said suspending agent consists essentially of about 0.7 to 1.5% hydrophobic colloidal silica and about 0.15 to 0.35% hydrophilic colloidal silica.

12. The aerosol antiperspirant composition of claim 11 wherein said composition contains substantially no polar agents or oil soluble emollient esters.

13. The aerosol antiperspirant composition of claim 12 wherein said hydrophobic colloidal silica has a BET surface area of about 100 $m^2/gm$ with about 70% of the surface hydroxyl groups methylated and said hydrophilic colloidal silica has a BET surface area of about 300 $m^2/gm$.

* * * * *

UNITED STATES PATENT AND TRADEMARK OFFICE
CERTIFICATE OF CORRECTION

PATENT NO. : 5,368,842
DATED : November 29, 1994
INVENTOR(S) : Barry P. Lederman, et al It is certified that error appears in the above-indentified patent and that said Letters Patent is hereby corrected as shown below:

Add the drawing sheet, consisting of Figs. 1, as shown on the attached pages.

Signed and Sealed this

Twenty-first Day of February, 1995

Attest:

BRUCE LEHMAN

Attesting Officer    Commissioner of Patents and Trademarks